(12) United States Patent
Pilutti et al.

(10) Patent No.: US 8,483,958 B2
(45) Date of Patent: Jul. 9, 2013

(54) USER CONFIGURABLE ONBOARD NAVIGATION SYSTEM CROSSROAD PRESENTATION

(75) Inventors: Thomas Edward Pilutti, Ann Arbor, MI (US); Davorin David Hrovat, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 330 days.

(21) Appl. No.: 12/972,638

(22) Filed: Dec. 20, 2010

(65) Prior Publication Data
US 2012/0158292 A1 Jun. 21, 2012

(51) Int. Cl.
*G08G 1/123* (2006.01)

(52) U.S. Cl.
USPC .......................................... 701/437; 340/988

(58) Field of Classification Search
USPC ................... 701/533, 437, 428, 23, 408, 469, 701/457, 301, 532, 25; 340/995.19, 988, 340/990, 989, 907, 929, 903
See application file for complete search history.

(56) References Cited

U.S. PATENT DOCUMENTS

| | | | |
|---|---|---|---|
| 4,937,751 A | 6/1990 | Nimura et al. |
| 5,177,685 A | 1/1993 | Davis et al. |
| 5,220,507 A | 6/1993 | Kirson |
| 5,275,474 A | 1/1994 | Chin et al. |
| 5,291,412 A | 3/1994 | Tamai et al. |
| 5,351,779 A | 10/1994 | Yamashita |
| 5,394,332 A | 2/1995 | Kuwahara et al. |
| 5,406,491 A | 4/1995 | Lima |
| 5,406,492 A | 4/1995 | Suzuki |
| 5,578,748 A | 11/1996 | Brehob et al. |
| 5,742,922 A | 4/1998 | Kim |
| 5,767,795 A | 6/1998 | Schaphorst |
| 5,790,973 A | 8/1998 | Blaker et al. |
| 5,848,364 A | 12/1998 | Ohashi |
| 6,005,494 A | 12/1999 | Schramm |
| 6,028,537 A | 2/2000 | Suman et al. |
| 6,101,443 A | 8/2000 | Kato et al. |
| 6,314,369 B1 | 11/2001 | Ito et al. |
| 6,374,177 B1 | 4/2002 | Lee et al. |
| 6,424,363 B1 | 7/2002 | Matsuba et al. |
| 6,424,888 B1 | 7/2002 | Sone et al. |
| 6,427,115 B1 | 7/2002 | Sekiyama |
| 6,427,117 B1 | 7/2002 | Ito et al. |

(Continued)

FOREIGN PATENT DOCUMENTS
WO  2008037471 A2  4/2008

OTHER PUBLICATIONS

Navigator—A Talking GPS Receiver for the Blind, Ryszard Kowalik and Stanislaw Kwasniewski, Gdansk University of Technology, 2004.

(Continued)

*Primary Examiner* — Thomas Black
*Assistant Examiner* — Luke Huynh
(74) *Attorney, Agent, or Firm* — Jennifer M. Stec; Brooks Kushman P.C.

(57) ABSTRACT

A computer-implemented method for road identification includes receiving a request at a vehicle computing system for a crossroad identification. The method also includes determining, via the vehicle computing system, a crossroad along a route-being-traveled corresponding to the request. The method further includes outputting, from the vehicle computing system to an output, the determined crossroad responsive to the request.

19 Claims, 4 Drawing Sheets

U.S. PATENT DOCUMENTS

| | | |
|---|---|---|
| 6,462,676 B1 | 10/2002 | Koizumi |
| 6,484,092 B2 | 11/2002 | Seibel |
| 6,484,093 B1 | 11/2002 | Ito et al. |
| 6,533,367 B1 | 3/2003 | Latarnik et al. |
| 6,574,538 B2 | 6/2003 | Sasaki |
| 6,691,025 B2 | 2/2004 | Reimer |
| 6,791,471 B2 | 9/2004 | Wehner et al. |
| 6,829,529 B2 | 12/2004 | Trefzer et al. |
| 6,834,229 B2 | 12/2004 | Rafiah et al. |
| 6,866,349 B2 | 3/2005 | Sauter et al. |
| 6,904,362 B2 | 6/2005 | Nakashima et al. |
| 7,053,866 B1 | 5/2006 | Mimran |
| 7,089,110 B2 | 8/2006 | Pechatnikov et al. |
| 7,113,107 B2 | 9/2006 | Taylor |
| 7,167,799 B1 | 1/2007 | Dolgov et al. |
| 7,243,134 B2 | 7/2007 | Bruner et al. |
| 7,369,938 B2 | 5/2008 | Scholl |
| 7,486,199 B2 | 2/2009 | Tengler et al. |
| 7,571,042 B2 | 8/2009 | Taylor et al. |
| 7,642,901 B2 | 1/2010 | Kato et al. |
| 7,653,481 B2 | 1/2010 | Tramel |
| 7,726,360 B2 | 6/2010 | Sato et al. |
| 7,818,380 B2 | 10/2010 | Tamura et al. |
| 7,822,380 B2 | 10/2010 | Wu |
| 7,822,546 B2 | 10/2010 | Lee |
| 7,826,945 B2 | 11/2010 | Zhang et al. |
| 7,920,969 B2 | 4/2011 | Mudalige et al. |
| 2001/0001847 A1 | 5/2001 | Hessing |
| 2002/0087262 A1 | 7/2002 | Bullock et al. |
| 2003/0040866 A1 | 2/2003 | Kawakami |
| 2003/0040868 A1 | 2/2003 | Fish et al. |
| 2003/0158652 A1 | 8/2003 | Friedrichs et al. |
| 2004/0021583 A1 | 2/2004 | Lau et al. |
| 2004/0117108 A1 | 6/2004 | Nemeth |
| 2005/0085956 A1 | 4/2005 | Losey |
| 2005/0144573 A1 | 6/2005 | Moody et al. |
| 2005/0159881 A1 | 7/2005 | Furukawa |
| 2006/0026335 A1 | 2/2006 | Hodgson et al. |
| 2006/0089788 A1 | 4/2006 | Laverty |
| 2006/0168627 A1 | 7/2006 | Zeinstra et al. |
| 2006/0172745 A1 | 8/2006 | Knowles |
| 2006/0184314 A1 | 8/2006 | Couckuyt et al. |
| 2006/0190164 A1 | 8/2006 | Glaza |
| 2006/0241857 A1 | 10/2006 | Onishi et al. |
| 2007/0005241 A1* | 1/2007 | Sumizawa et al. ............ 701/211 |
| 2007/0038362 A1 | 2/2007 | Gueziec |
| 2007/0050248 A1 | 3/2007 | Huang et al. |
| 2007/0093955 A1 | 4/2007 | Hughes |
| 2007/0104224 A1 | 5/2007 | Conner et al. |
| 2007/0143482 A1 | 6/2007 | Zancho |
| 2007/0143798 A1 | 6/2007 | Jira et al. |
| 2007/0198172 A1 | 8/2007 | Sumizawa et al. |
| 2007/0203643 A1 | 8/2007 | Ramaswamy et al. |
| 2007/0203646 A1 | 8/2007 | Diaz et al. |
| 2007/0213092 A1 | 9/2007 | Geelen |
| 2007/0273624 A1 | 11/2007 | Geelen |
| 2007/0290839 A1 | 12/2007 | Uyeki et al. |
| 2008/0065318 A1 | 3/2008 | Ho |
| 2008/0147308 A1 | 6/2008 | Howard et al. |
| 2008/0195305 A1 | 8/2008 | Jendbro et al. |
| 2008/0228346 A1 | 9/2008 | Lucas et al. |
| 2009/0143934 A1 | 6/2009 | Motonaga et al. |
| 2009/0196294 A1 | 8/2009 | Black et al. |
| 2009/0254266 A1 | 10/2009 | Altrichter et al. |
| 2009/0259354 A1 | 10/2009 | Krupadanam et al. |
| 2009/0326797 A1 | 12/2009 | Tengler et al. |
| 2009/0326801 A1 | 12/2009 | Johnson et al. |
| 2010/0010732 A1 | 1/2010 | Hartman |
| 2010/0048184 A1 | 2/2010 | Kim |
| 2010/0088018 A1* | 4/2010 | Tsurutome et al. ........... 701/201 |
| 2010/0088029 A1 | 4/2010 | Hu et al. |
| 2010/0094550 A1 | 4/2010 | Tsurutome et al. |
| 2010/0174485 A1 | 7/2010 | Taylor et al. |
| 2010/0191463 A1 | 7/2010 | Berry et al. |
| 2010/0198508 A1 | 8/2010 | Tang |
| 2010/0217482 A1 | 8/2010 | Vogel et al. |
| 2010/0241342 A1 | 9/2010 | Scalf et al. |
| 2010/0245123 A1 | 9/2010 | Prasad et al. |
| 2011/0004523 A1 | 1/2011 | Giuli et al. |
| 2011/0046883 A1 | 2/2011 | Ross et al. |
| 2011/0166774 A1 | 7/2011 | Schunder |
| 2011/0255481 A1 | 10/2011 | Sumcad et al. |
| 2012/0004841 A1 | 1/2012 | Schunder |
| 2012/0029806 A1 | 2/2012 | Scalf et al. |
| 2012/0029807 A1 | 2/2012 | Schunder et al. |
| 2012/0041673 A1 | 2/2012 | Vandivier et al. |
| 2012/0053825 A1 | 3/2012 | Schunder |

OTHER PUBLICATIONS

Speech-Enabled Web Services for Mobile Devices, M. Hu, Z. Davis, S. Prasad, M. Schuricht, P.M. Melilar-Smith and L.E. Moser, Department of Electrical and Computer Engineering, University of California, Santa Barbara, CA 93106.

Kermit Whitfield, "A hitchhiker's guide to the telematics ecosystem", Automotive Design & Production, Oct. 2003, http://findarticles.com, pp. 1-3.

Ford Motor Company, "Navigation System: SYNC," Owner's Guide Supplement, SYNC Version 1 (Jul. 2007).

Ford Motor Company, "SYNC," Owner's Guide Supplement, SYNC Version 1 (Nov. 2007).

Ford Motor Company, "Navigation System: SYNC," Owner's Guide Supplement, SYNC Version 2 (Oct. 2008).

Ford Motor Company, "SYNC," Owner's Guide Supplement, SYNC Version 2 (Oct. 2008).

Ford Motor Company, "Navigation System: SYNC," Owner's Guide Supplement, SYNC Version 3 (Jul. 2009).

Ford Motor Company, "SYNC," Owner's Guide Supplement, SYNC Version 3 (Aug. 2009).

Findlater et al., Impact of Screen Size on Performance, Awareness, and User Satisfaction with Graphical User Interfaces, Association for Computing Machinery (ACM), Apr. 5-10, 2008, pp. 1247-1256, see Fig. 1.

Garmin Garage, Follow the Leader, www.garmin.com/garmin/cms/site/us.

TomTom, portable car navigation systems, http://www.tomtom.com, Feb. 6, 2009.

MapQuest Maps—Driving Directions—Map, http://www.mapquest.com, Aug. 25, 2009.

Multi-Modal Navigation Tools, TDM Encyclopedia, Jan. 26, 2010.

Google Maps Finally Adds Bike Routes, Mary Catherine O'Connor, Mar. 10, 2010, printed from www.wired.com/autopia/2010/03/google-maps-for-bikes/.

POI Along Route Qs, Printed from http://www.tomtomforums.com, printed Jul. 30, 2010.

Difficult POI search in Streets & Trips, printed from http://www.laptopgpsworld.com/3520-difficult-poi-search-streets-tips, printed Jul. 30, 2010.

http://www.rated4stars.com/html/gps-saves-gas.html.

http://www.gps.cx/index.php?c=1&n=493964&i=B001LTHONU&x=GPS_Buddy_FE01US_Fuel_Economy_Software_Package.

http://www.gpsmagaziine.com/2009/02/hands-on_with_garmins_new_ecor.php (Feb. 2009).

http://www.nrel.gov/vehiclesandfuels/vsa/pdfs/42557.pdf (Apr. 2008).

http://green.autoblog.com/2009/03/05/sentience-research-vehicle-shows-how-tons-of-data-can-save-milli/ (Mar. 2009).

http://reviews.cnet.com18301-13746_7-10189749-48.html.

* cited by examiner

USER CONFIGURABLE ONBOARD NAVIGATION SYSTEM CROSSROAD PRESENTATION

BACKGROUND

GPS devices are becoming more prevalent in a variety of modes. Many vehicles come equipped with onboard navigation systems or onboard navigation capability. Typically, these systems will either display a route to be traveled, along with a series of directions, or they will audibly recite directions as a driver is en route to a destination.

Portable GPS devices and even some cellular phones or other wireless devices may also be used to provide directions, again, providing the directions in a visual or audible manner.

Typically, when interacting with these devices, a user will input a destination location. Using the present GPS coordinates of the vehicle, a routing engine will determine a route to the destination location, according to one or more predefined parameters (e.g., without limitation, fastest route, avoiding highways, avoiding toll roads, avoiding dirt roads, etc.).

In the most common manner of operation, the devices instruct the user when to turn (left, right, bear left, bear right, sharp left, sharp right, etc.). The warnings on when to turn are usually given some distance ahead of the turn, and may be repeated a number of times until the turn is to be made.

In many of these systems, however, little attention is given to, for example, crossroads along a route that are not taken as part of the route. For example, as a user approaches a particular turn along an audibly (but not visually) provided route, the user will typically only be given the instruction for when the turn occurs. In the audible-only systems, the user will not typically receive any data regarding roads along the route on which the user is not presently traveling or onto which the user is being instructed to turn.

Even with visual-based systems, cross-road names may not be displayed, and the user is provided with little, if any, information regarding cross-roads, unless the user inadvertently turns on to one of those roads (thus making the road part of the "new" route).

SUMMARY

In a first illustrative embodiment, a computer-implemented method for road identification includes receiving a request at a vehicle computing system for a crossroad identification. The method also includes determining, via the vehicle computing system, a crossroad along a route-being-traveled corresponding to the request. Finally the method includes outputting, from the vehicle computing system to an output, the determined crossroad responsive to the request.

In a second illustrative embodiment, a computer-implemented method includes determining, via a vehicle computing system (VCS), a classification of road on which a vehicle is traveling. The illustrative method also includes setting a crossroad identification level in the VCS based at least in part on the determined road classification. The method further includes receiving, at the VCS, a request for crossroad identification.

The illustrative method also includes determining, via the VCS, a crossroad corresponding to the request and the set crossroad identification level. Finally the method includes outputting, from the VCS to an output, the determined crossroad.

In a third illustrative embodiment, an apparatus includes receiving programmed logic circuitry to receive a request at a vehicle computing system for a crossroad identification. The apparatus also includes determining programmed logic circuitry to determine, via the vehicle computing system, a crossroad along a route-being-traveled corresponding to the request. Finally, this apparatus includes outputting programmed logic circuitry to output, from the vehicle computing system to an output, the determined crossroad responsive to the request.

DETAILED DESCRIPTION

Figure 1:
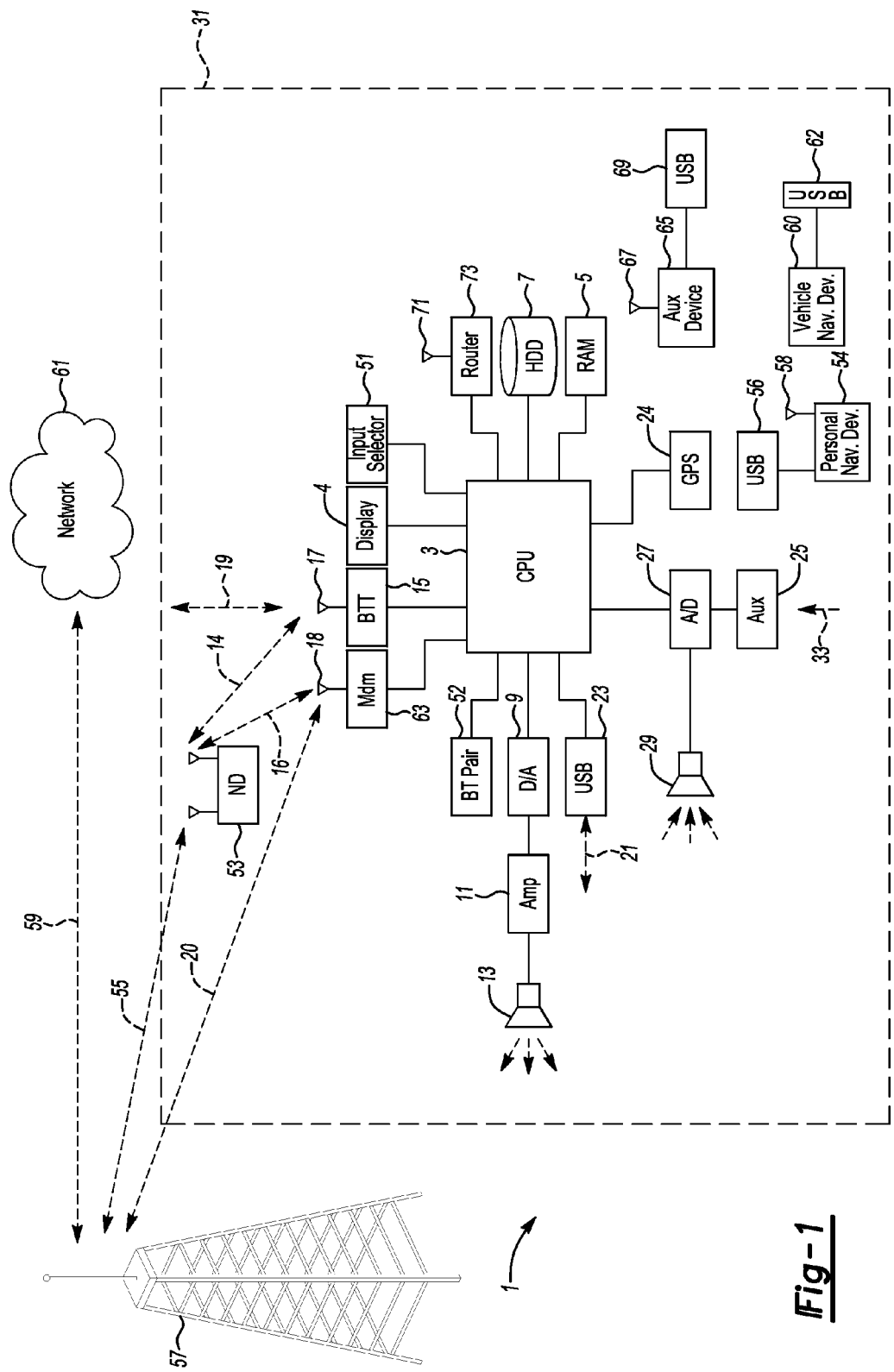
FIG. 1 illustrates an example block topology for a vehicle based computing system.

FIG. 1 illustrates an example block topology for a vehicle based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, audible speech and speech synthesis.

In the illustrative embodiment 1 shown in FIG. 1, a processor 3 controls at least some portion of the operation of the vehicle-based computing system. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory.

The processor is also provided with a number of different inputs allowing the user to interface with the processor. In this illustrative embodiment, a microphone 29, an auxiliary input 25 (for input 33), a USB input 23, a GPS input 24 and a BLUETOOTH input 15 are all provided. An input selector 51 is also provided, to allow a user to swap between various inputs. Input to both the microphone and the auxiliary connector is converted from analog to digital by a converter 27 before being passed to the processor.

Outputs to the system can include, but are not limited to, a visual display 4 and a speaker 13 or stereo system output. The speaker is connected to an amplifier 11 and receives its signal from the processor 3 through a digital-to-analog converter 9. Output can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., cell phone, smart phone, PDA, or any other device having wireless remote network connectivity). The nomadic device can then be used to communicate 59 with a network 61 outside the vehicle 31 through, for example, communication 55 with a cellular tower 57. In some embodiments, tower 57 may be a WiFi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device).

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example).

If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., WiFi) or a WiMax network.

In one embodiment, incoming data can be passed through the nomadic device via a data-over-voice or data-plan, through the onboard BLUETOOTH transceiver and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58; or a vehicle navigation device 60, having a USB 62 or other connection, an onboard GPS device 24, or remote navigation system (not shown) having connectivity to network 61.

Further, the CPU could be in communication with a variety of other auxiliary devices 65. These devices can be connected through a wireless 67 or wired 69 connection. Also, or alternatively, the CPU could be connected to a vehicle based wireless router 73, using for example a WiFi 71 transceiver. This could allow the CPU to connect to remote networks in range of the local router 73. Auxiliary device 65 may include, but are not limited to, personal media players, wireless health devices, portable computers, and the like.

Figure 2:
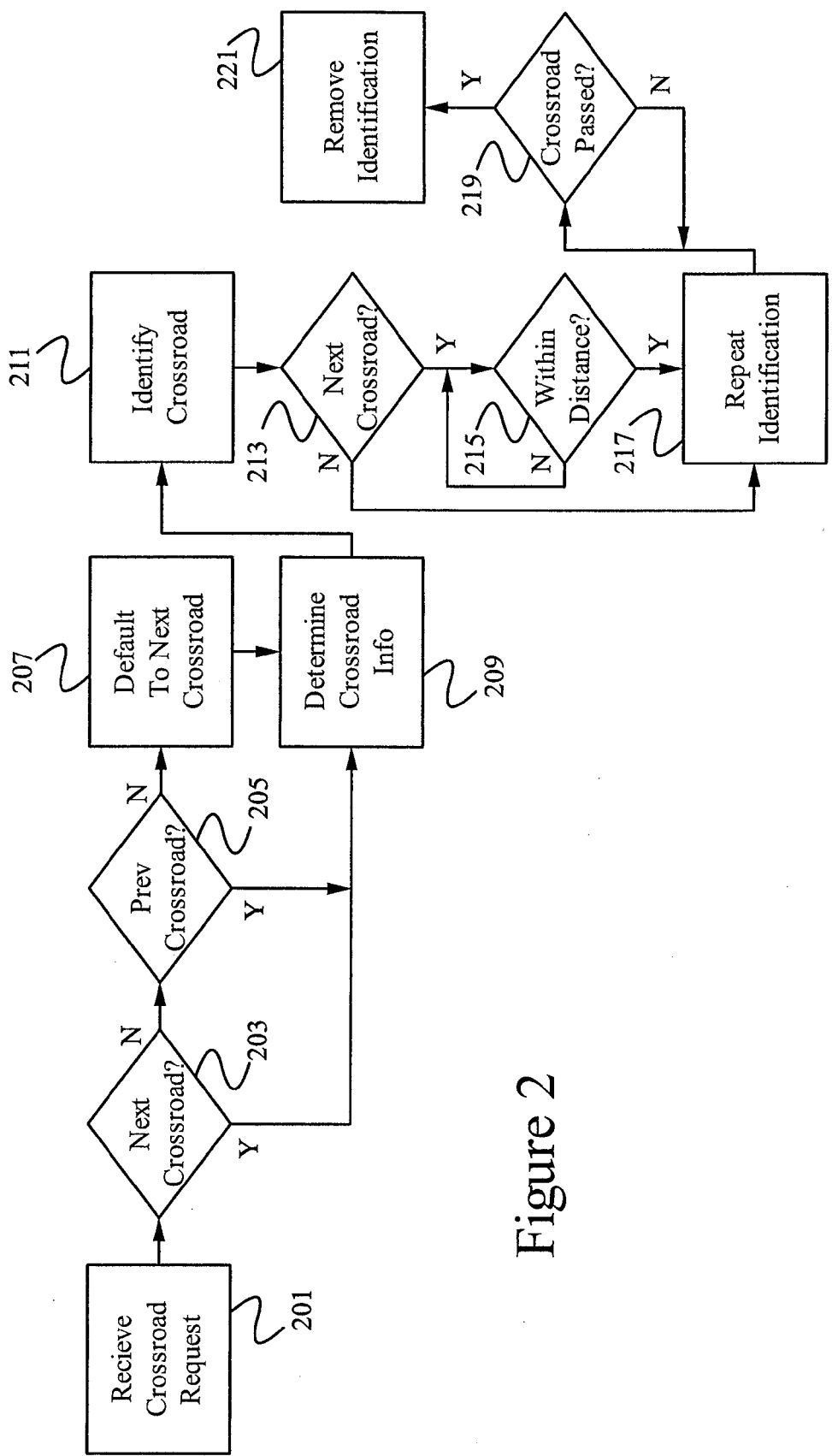
FIG. 2 shows an illustrative example of processing a user request for crossroad identification.

In a first illustrative embodiment, shown in FIG. 2, a vehicle navigation (or computing) system receives a request for identification of a crossroad along a route-being-traveled 201. Although not necessary, the user may identify the request as a "next" crossroad request 203 or a "previous" crossroad request (e.g., without limitation, the crossroad most recently passed) 205.

In this illustrative embodiment, if no identification of "next" or "previous" is provided, then the system will assume that the user is requesting information regarding the next upcoming crossroad along the route 207.

Once it is determined for which crossroad the user is requesting information, a vehicle navigation system (or computing system, or off-board remote routing system, etc) may examine a pre-stored map to determine the requested crossroad information 209.

In this illustrative embodiment, the system provides the identification in two instances. First, in response to the query, regardless of the user's present location, the system identifies the requested crossroad 211 (in this embodiment the crossroad is identified upon request, although it is possible that identification to the user may be delayed until a later point). This identification can be done audibly or visually (assuming the system has display capability). Additionally, in this illustrative embodiment, if the request is for an upcoming crossroad 213, then if (or once) the user is within a predetermined distance from the crossroad 215, the identification will be repeated (or fixedly displayed) 217. Once the user has passed the crossroad 219, the identification ceases 221.

The repeating of the identification may be in the form of one or more audible prompts provided at some series of intervals, it may be an audible prompt provided once (for the second time), or it may be a persistent display on a visual map on a vehicle navigation display. Of course, such a secondary display/vocalization may also be omitted if desired.

In one illustrative embodiment, if a visual display is available for use by the vehicle computing system, a requested crossroad name may be displayed in a highlighted or otherwise enhanced manner. Alternatively, the crossroad name may be displayed in a pop-up window, or otherwise distinguished from the general map data being displayed. Of course, the road name may also be displayed in conjunction with the road on the displayed map, such as being displayed along-side the road (or having an identifier from the road name pointing or connecting to the road).

Finally, in this illustrative embodiment, once the road has been passed by the driver, the display is removed/ended 219 (or an enhanced display is rendered ordinary). This may aid the driver in keeping track of a present location on a map, especially if the level of the view is zoomed out to an extent where the vehicle position may not be readily apparent (due, for example, to the icon representing the vehicle remaining large whilst the display of streets past which the vehicle is traveling has been reduced and become somewhat crowded).

Figure 3:
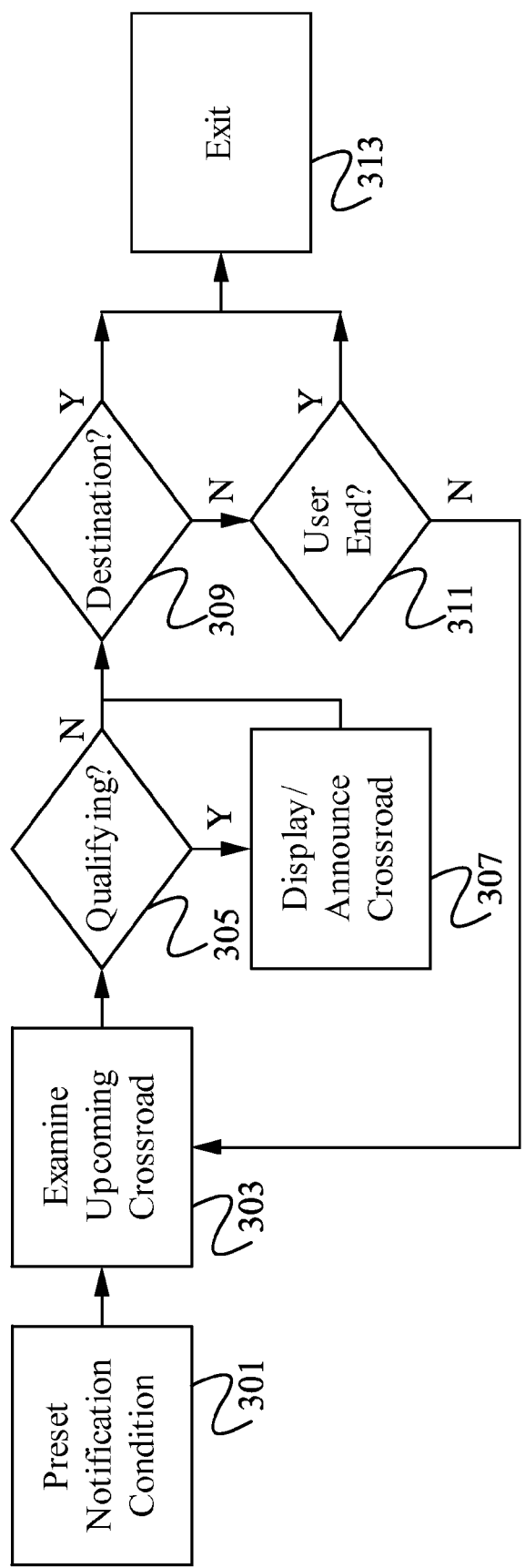
FIG. 3 shows an illustrative example of automatic provision of crossroad information for at least one category of road.

In yet another illustrative example, discussed with more detail with respect to FIG. 3, a "level" of crossroad is set or otherwise determined to be the identification level. In such an embodiment, a request for an upcoming crossroad may (based on a dynamic or user-initiated setting) ignore certain roads and identify, for example, the next "major" (or other selected road level) crossroad. Similarly, in this scenario, the last "major" crossroad would be identified if a "previous" request was initiated.

FIG. 3 shows an illustrative example of automatic provision of crossroad information for at least one category of road. In this illustrative embodiment, it is assumed that a system of road categorization is accessible by a determination engine (located, for example, without limitation, in a vehicle computing system, a remote server, etc.). For example, one common system of classification uses five categories for roads, based on the speed limits of the roads. Roads in a certain speed range fall into a particular classification. While not failproof, such a system will typically serve to distinguish major roads from smaller local streets, since speed limits tend to typically be slower on local streets. Other classification systems may also be applied, as desired.

For example, in another illustrative embodiment, intersection classification may be available. Either using a ranking system as described above, classifications such as "traffic signal", "traffic sign", etc. or some other suitable system, a determination engine may be able to distinguish intersection types.

Figure 4:
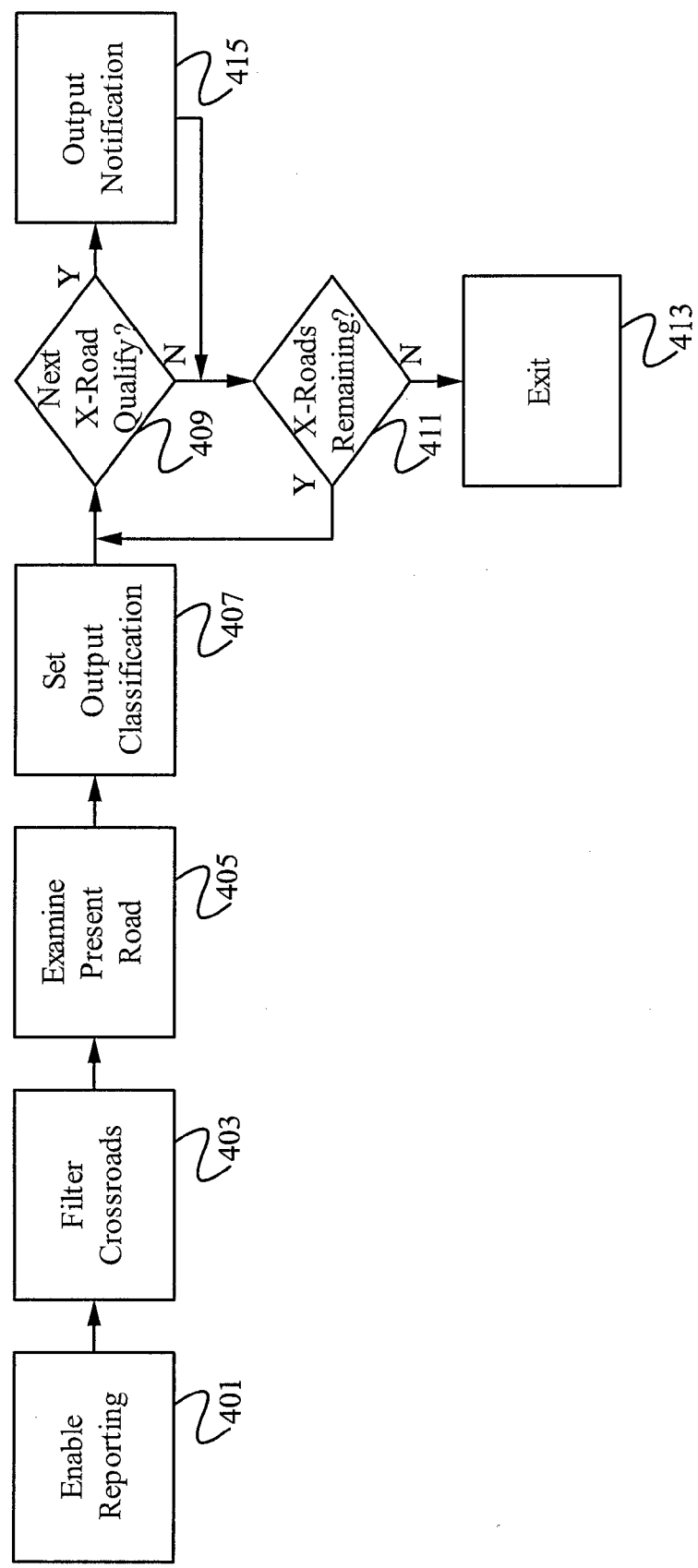
FIG. 4 shows an illustrative example of a system for dynamically presenting a level of crossroad information based on at least one predetermined condition.

Based on some determined system of classification, a user can set (or a system can dynamically select, as discussed with regards to FIG. 4) a level of detail. For example, a user may only wish to know major crossroads in a given area. If a user is traveling, for example, in a car filled with distractions, such as noisy children, the user may not be able to focus on the navigation system during the trip. Thus, it may be useful, especially when traveling in an area that is somewhat known, to know when a major crossroad prior to a turn is reached.

In this example, based on a user-request or a predefined setting (such as, but not limited to, "identify all crossroads of X type"), a user may be notified just prior to and/or just after crossing a crossroad of X type along a route. This may make it easier for a user to be aware that a turn is upcoming, without necessitating that the user focus solely on the navigation system. This may also be useful, for example, in hectic traffic, when weather conditions are somewhat obscuring the visibility along a route, when traveling at night, etc.

Sometimes, a user will receive verbal instructions from a person at the destination as well e.g.—"we're the second right after Telegraph road", and it may be useful to know when Telegraph road is reached so that the user can prepare to make a turn. The user may find this more useful than instructions from the GPS such as "turn right in three hundred meters", especially if there are a densely packed network of small and/or poorly marked side streets following a major intersection.

This information could similarly be useful if the destination is on the road on which the user is traveling, and the user knows that the destination is "just past Telegraph road on the right" for example. Thus, when Telegraph road is approached/reached/passed, the user can begin scanning the right-hand side of the road for a destination. Such information may be especially useful if the destination is in a strip mall or the like, where the GPS may only have an approximate, and not a precise, location available.

In the illustrative embodiment shown in FIG. 3, a user presets a condition for crossroad notification 301. As previously noted, this could be a road classification (or type), an intersection/traffic control feature notification (e.g., "name all crossroads having lights", or the road type could be classified based on traffic control feature), or any other suitable variation between roads. Additionally or alternatively, the user could request that all crossroads be named/displayed.

Once the road type has been set, a determination process (located onboard the vehicle or remotely) examines each crossroad 303. If the crossroad qualifies for reporting 305, then the system will display and/or announce the crossroad 307 in accordance with the available features and/or system settings.

If a destination has been reached 309, then the process ends. Similarly, if the user disables the feature 311, then the process ends 313. Otherwise, a next crossroad is examined as it is approached 303.

In this manner, the system can automatically report some types or all crossroads without requiring a user prompt. This is just one manner in which the process may be implemented.

Next crossroads may be examined by the system at any distance from the crossroad, although the system may not elect to report the next crossroad until the user is within a certain distance of the crossroad (e.g., without limitation, a projected visible distance). Similarly, display/output of a particular crossroad may be ceased after the crossroad has been passed.

FIG. 4 shows an illustrative example of a system for dynamically presenting a level of crossroad information based on at least one predetermined condition.

In this illustrative embodiment, either automatic or per-request crossroad reporting may be enabled 401. In this embodiment, the system has been instructed to filter crossroads based on dynamic conditions 403. In one example, the filter is based at least in part on the road type on which the user is traveling.

In this illustrative example, if the user is traveling on, for example, a highway, then it may be the case that only exit roads are announced/displayed (ignoring overpasses without exits). If the user exits the highway and passes into a suburban area, then the announcement/display may pass down to a surface street level (or at least a slower class of road than was previously announced/displayed).

Whether the reporting is automatic or by request, the "next" or "previous" road that is reported is determined, in this illustrative example, by the classification filter.

Once the filter has been enabled 403, a decision process examines the type of road on which the user is presently traveling 405 and sets a level of output based on that road's classification 407. Then, the process examines a next crossroad (or previous, if so requested) and determines if the next crossroad qualifies for output 409. If the next crossroad does not qualify, the system checks to see if any crossroads remain between a present location and a final destination (assuming that further crossroads are to be output) 411. If no crossroads remain, the process exits 413. If crossroads remain, the process returns to examining a next crossroad 409.

If a crossroad qualifies for reporting, then the crossroad is output at an appropriate time 415 in a manner consistent with available features and/or vehicle settings. As with the previous cases, this can be a visual or audible output, and the system may cease/remove the output one the crossroad has been passed.

In yet a further illustrative embodiment, a user may request notification when a specific crossroad is being approached. The requested crossroad can then be visually or audibly highlighted as the user approaches (or passes) the requested crossroad.

Although the invention has been described in terms of illustrative embodiments, these are intended to provide examples and not to limit the scope of the invention.

What is claimed:

1. A computer-implemented method for road identification comprising:

receiving a request at a vehicle computing system for a crossroad identification including a request to identify cross-roads of a certain type, wherein the type is dynamically identified by the request;

determining, via the vehicle computing system, a crossroad along a route-being-traveled corresponding to the request; and outputting, from the vehicle computing system to an output, the determined crossroad responsive to the request.

2. The method of claim 1, wherein the request is predefined for at least a single route and is responded to via the vehicle computing system for a duration of the at least a single route.

3. The method of claim 1, wherein the crossroad type is defined by a predetermined ranking system.

4. The method of claim 1, wherein the crossroad type is defined by a traffic control feature.

5. The method of claim 4, wherein the traffic control feature is a stop sign.

6. The method of claim 4, wherein the traffic control feature is a stop light.

7. The method of claim 1, wherein the crossroad type is predefined within the vehicle computing system.

8. The method of claim 1, wherein the request includes a specific crossroad name.

9. The method of claim 1, wherein the outputting further includes outputting the determined crossroad immediately following the request.

10. The method of claim 1, wherein the outputting further includes outputting the determined crossroad when the vehicle is within a predefined proximity to the crossroad.

11. The method of claim 10, wherein the outputting is ceased after the vehicle has passed the crossroad if the request was for a crossroad not yet passed by the vehicle at the time of the request.

12. The method of claim 1, wherein the request is for a next crossroad.

13. The method of claim 1, wherein the request is for a previous crossroad.

14. The method of claim 1, wherein the outputting is performed on a visual display.

15. The method of claim 14, wherein the crossroad name is displayed in an enhanced manner on the visual display.

16. The method of claim 15, wherein the enhanced manner includes displaying the name of the crossroad in a font larger than that used to display other road names.

17. The method of claim 15, wherein the enhanced manner includes displaying the name of the crossroad in a pop-up window.

18. The method of claim 1, wherein the outputting is performed over an audio output.

19. A computer-implemented method comprising:

determining, via a vehicle computing system (VCS), a classification of road on which a vehicle is traveling;

setting a crossroad identification level in the VCS based at least in part on the determined road classification;

receiving, at the VCS, a request for crossroad identification including a request to identify cross-roads of a certain type, wherein the type is dynamically identified by the request;

determining, via the VCS, a crossroad corresponding to the request and the set crossroad identification level; and outputting, from the VCS to an output, the determined crossroad.

* * * * *